(12) United States Patent
Shanbrom

(10) Patent No.: US 8,389,687 B2
(45) Date of Patent: Mar. 5, 2013

(54) POLYVINYLPYRROLIDONE CRYOPRECIPITATE EXTRACTION OF CLOTTING FACTORS

(75) Inventor: Edward Shanbrom, Santa Ana, CA (US)

(73) Assignee: Shanbrom Technologies, LLC, Ojai, CA (US)

( * ) Notice: Subject to any disclaimer, the term of this patent is extended or adjusted under 35 U.S.C. 154(b) by 627 days.

(21) Appl. No.: 11/932,958

(22) Filed: Oct. 31, 2007

(65) Prior Publication Data

US 2008/0281081 A1 Nov. 13, 2008

Related U.S. Application Data

(63) Continuation-in-part of application No. 10/280,501, filed on Oct. 25, 2002, now Pat. No. 7,297,716, which is a continuation-in-part of application No. PCT/US02/03996, filed on Feb. 7, 2002, which is a continuation-in-part of application No. 09/694,178, filed on Oct. 23, 2000, now Pat. No. 6,881,731, and a continuation-in-part of application No. 09/778,681, filed on Feb. 7, 2001, now Pat. No. 6,541,518.

(60) Provisional application No. 60/278,496, filed on Mar. 23, 2001.

(51) Int. Cl.
*C07K 1/14* (2006.01)
*A61K 35/14* (2006.01)
*A61K 47/30* (2006.01)

(52) U.S. Cl. ...... 530/383; 530/422; 530/427; 514/772.3

(58) Field of Classification Search .................. None
See application file for complete search history.

(56) References Cited

U.S. PATENT DOCUMENTS

| | | | |
|---|---|---|---|
| 3,560,475 A | 2/1971 | Fekete | |
| 3,631,018 A | 12/1971 | Shanbrom | |
| 3,803,115 A | 4/1974 | Fekete et al. | |
| 4,025,654 A | 5/1977 | Farhadieh | |
| 4,069,219 A | 1/1978 | Weier | |
| 4,086,218 A | 4/1978 | Shanbrom et al. | |
| 4,305,871 A | 12/1981 | Shanbrom | |
| 4,327,086 A | 4/1982 | Fukushima et al. | |
| 4,359,463 A * | 11/1982 | Rock .............. | 424/529 |
| 4,925,665 A | 5/1990 | Murphy | |
| 4,977,246 A | 12/1990 | Lee et al. | |
| 5,196,428 A | 3/1993 | Meanwell | |
| 5,459,030 A | 10/1995 | Lin et al. | |
| 5,656,591 A | 8/1997 | Tomita et al. | |
| 5,660,731 A | 8/1997 | Piechocki et al. | |
| 5,770,704 A | 6/1998 | Godowski | |
| 5,875,799 A | 3/1999 | Petrus | |
| 5,985,260 A | 11/1999 | Shanbrom | |
| 6,037,116 A | 3/2000 | Wiggins et al. | |
| 6,403,381 B1 | 6/2002 | Mann et al. | |

FOREIGN PATENT DOCUMENTS

| | | |
|---|---|---|
| DE | 3316464 A1 | 11/1984 |
| EP | 188008 A2 | 7/1986 |
| EP | 0272551 A2 | 6/1988 |
| RU | 2033611 C1 | 4/1995 |
| WO | WO-8900006 A1 | 1/1989 |
| WO | WO-93/04678 A1 | 3/1993 |
| WO | WO-93/21933 A1 | 11/1993 |
| WO | WO-96/18292 A1 | 6/1996 |
| WO | WO-9822151 A1 | 5/1998 |

OTHER PUBLICATIONS

Casillas, G., et al. 1982 Brit J Haemat 50: 665-672.*
Vermeer, C., et al. 1976 Vox Sang 30: 1-22.*
Preston, A.E. 1967 Brit J Haemat 13: 42-59.*
Zuber, T., et al. 1982 British Journal of Haematology 52: 517-518.*
J.L Veron, et al., Combined Cohn/chromatography pruification process for the manufacturing of high purity human albumin from plasma, 1993, pp. 183-188.
K. Pederson, Inhibition of bacterial haemolysis on blood agar medium by oxalate or citrate used as anticoagulants, 1973, pp. 384.
D. Thompson, et al. Fibrin Glue: A review of its preparation, efficay, and adverse effects as a tropical hemostat, 1988, pp. 946-952.
S. Arrighi, et al., Process for the isolation of highly purified factors IX, X and II from prothrombin complex or human plasma, 1995, pp. 183-188.
Oldurova, Problemy Gematol, i Perelivan. Krovi., Jun. 1961 No. 11, 52-55.

\* cited by examiner

*Primary Examiner* — Marsha Tsay
(74) *Attorney, Agent, or Firm* — Venable LLP; Stefan J. Kirchanski, Esq.

(57) ABSTRACT

Blood collection, processing and transfer leads to the separation of discrete fractions by adding additional citrate (trisodium citrate) to bring the citrate concentration to 10%-15% w/v thereby leading to enhanced yield and purity of cryoprecipitate. The improved cryoprecipitate then yields concentrated clotting factors by an improved extraction process which uses polyvinyl pyrollidone to reduce the extraction of fibrinogen. Following extraction the remaining cryoprecipitate can advantageously be formed into a fibrin fabric used in surgeries and in the treatment of wounds.

9 Claims, 1 Drawing Sheet

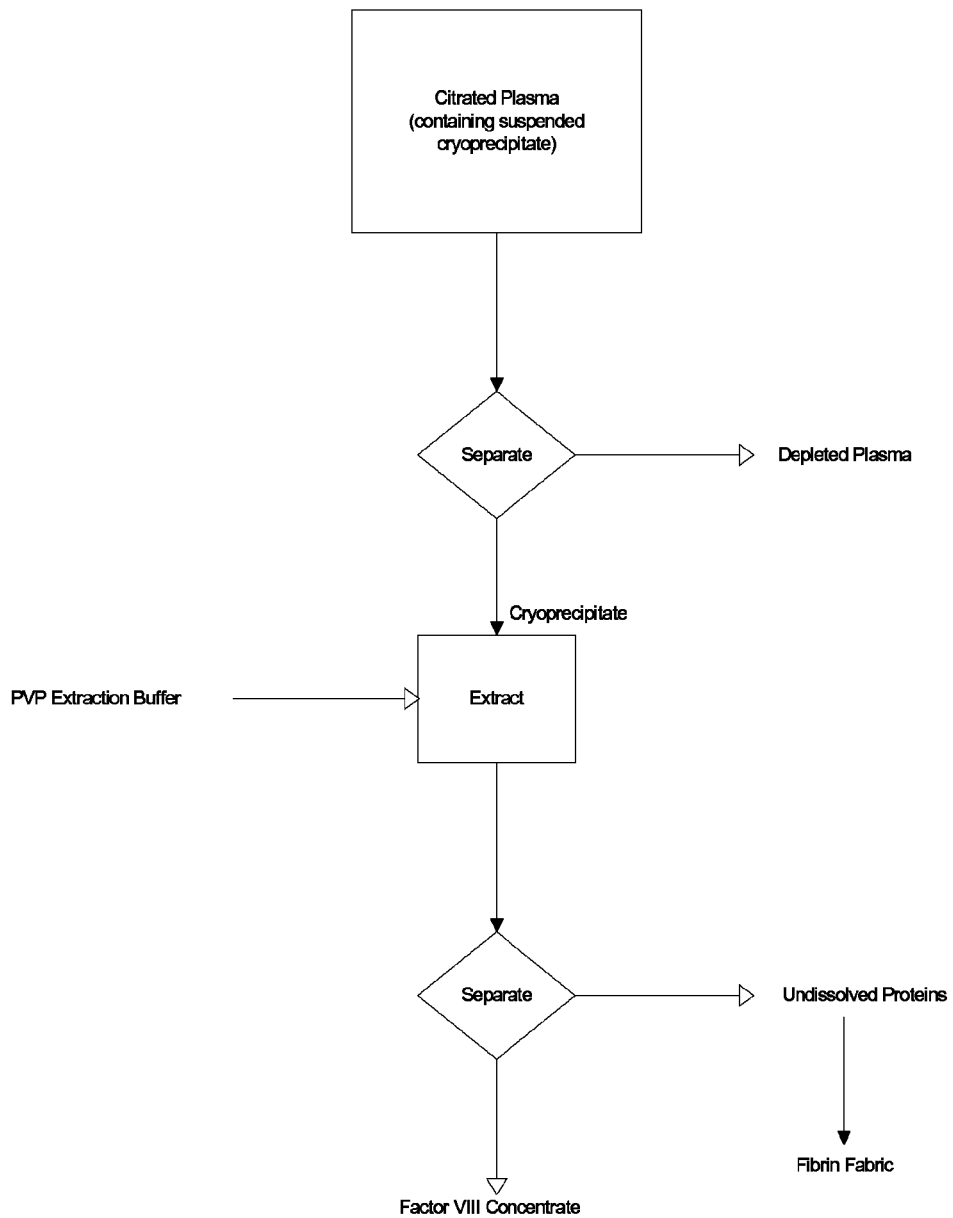

POLYVINYLPYRROLIDONE CRYOPRECIPITATE EXTRACTION OF CLOTTING FACTORS

RELATED APPLICATIONS

The present application is a continuation-in-part of copending U.S. patent application Ser. No. 10/280,501, filed Oct. 25, 2002, now U.S. Pat. No. 7,297,716, which in turn was a continuation-in-part of International Patent Application No. PCT/US02/03996 filed Feb. 7, 2002, designating the United States, which in turn was continuation-in-part of U.S. patent application Ser. No. 09/694,178 filed Oct. 23, 2000, now U.S. Pat. No. 6,881,731, and U.S. patent application Ser. No. 09/778,681 filed on 7 Feb. 2001 now U.S. Pat. No. 6,541,518, and U.S. Patent Application Ser. No. 60/278,496 filed 23 Mar. 2001. To the extent allowable, all these applications are incorporated by reference herein.

BACKGROUND OF THE INVENTION

1. Area of the Art

The present invention relates to the art of producing coagulation factor concentrates from blood plasma.

2. Description of the Prior Art

There are a number of medical indications for administration of "clotting" or "coagulation" factors from human blood. These factors are proteins that cause the clotting of blood to staunch bleeding from wounds, etc. Individuals with any of a series of genetic abnormalities affecting the proteins responsible for blood coagulation are afflicted with a disease (hemophilia) in which the blood fails to clot normally, subjecting the individual to the danger of uncontrolled bleeding. For many years, this condition has been treated by administering concentrates of the missing or defective proteins. Many clotting factors are synthesized in the liver so that victims of liver disease are also in need of augmentation of their clotting factors.

While some of the clotting factors are currently produced by means of biotechnology, at this time there is still no cost effective method of artificially manufacturing all of these proteins or these proteins in sufficient quantities. Further, the "artificially produced" factors made by recombinant and related technologies tend to have a shorter half-life in circulation. In addition, many of the "minor" clotting factors are not yet (and may never be) available from biotechnology sources and so must be purified from donated human blood. Also, there is often a synergy between factors whereby a single administered recombinant factor may not be as effective as a natural mixed fraction fractionated from collected blood plasma. In Third World countries the biotechnology products are generally either not available or are prohibitively expensive. Therefore, much of the supply of anti-hemophilia factor (AHF, also known as Factor VIII), and other blood clotting factors are prepared from pooled human plasma in the Third World.

The basic methods for preparing clotting factor concentrates from blood have not changed greatly over the last few decades. Generally, a concentrate of clotting factors is produced from pooled plasma by an initial cryoprecipitation step. The plasma is frozen and then thawed. During the freezing process certain proteins precipitate to form a "cryoprecipitate." Various additives such as ethanol and/or polyethylene glycol may be added to enhance the efficiency of the cryoprecipitation step. The present inventor has found that sodium citrate can advantageously used as an additive to enhance cryoprecipitate production (see U.S. Pat. No. 6,541, 518 the contents of which are hereby incorporated by reference). Following cryoprecipitation, it is usual to extract clotting factors from the cryoprecipitate. The cryoprecipitate is usually extracted with water or buffer in the cold. Under such conditions clotting factors and some other proteins are dissolved out of the precipitate yielding a crude clotting factor mixture. This crude mixture is usually further purified by means of additional precipitation steps or by chromatographic methods, and most recently by methods using monoclonal antibodies. For additional information on the basic techniques of clotting factor purification and the history of the development of these methods, the reader is directed to U.S. Pat. Nos. 3,560,475, 3,631,018, 3,682,881, 4,069,216, and 4,305,871 and 5,770,704 by the present inventor, the contents of which are incorporated herein by reference, and the references cited therein.

SUMMARY OF THE INVENTION

Derivatives of simple carboxylic acids, particularly trisodium citrate and other citric acid salts (hereinafter "citrate") have been shown to be unexpectedly effective agents for enhancing the production of blood clotting factors. It is believed that other small carboxylic acids, isocitric acid in particular, show similar properties. However, to date most of the tests have been made with citric acid and its salts. Addition of citrate to plasma, especially at concentrations between 10 and 15% by weight, does not apparently damage labile proteins. Most significantly, added citrate causes a dramatic increase in the weight of cryoprecipitate that can be produced from plasma by the usual procedures. The majority of the major clotting factors are greatly concentrated in the resulting cryoprecipitate—to the result that the supernatant contains little if any of these clotting factors. It is apparent that increasing the amount of citrate in blood bags so that the final concentration will be preferably 10-15%) by weight results in plasma that can be used to produce enriched cryoprecipitate. The added citrate can also help eliminate or suppress contaminating microorganisms and can itself be removed later by ion exchange or similar methods well known in the art.

The added citrate enhances the yield and purity of cryoprecipitate. Not only does added citrate increase the amount of cryoprecipitate; it simplifies the process by eliminating the requirement for freezing. Furthermore, added citrate can inhibit the activation or denaturation of blood components such as plasma proteins and/or facilitate the removal of the activated or denatured components and improves the safety and efficacy of end products. Citrate is used in increased quantities, preferably 10-15% weight by volume, over the level traditionally employed for anticoagulation in one or other collection or processing bag. A less preferred alternative is to add the extra citrate when thawing frozen plasma that contains the tradition amount of citrate (0.4% by weight).

Once the enriched cryoprecipitate is produced according to the inventive method highly purified Factor VIII can be extracted from that cryoprecipitate. The cryoprecipitate is extracted with cold (below about 10° C.) solution containing at least 2.5% polyvinylpyrrolidone to yield a clotting factor concentrate. Compared to extraction with plain saline or water, this procedure dissolves less of the fibrinogen and other proteins found in the cryoprecipitate. Therefore, this improved extraction can be used on plasma from a single donor or from a limited donor pool to make a useable clotting factor concentrate under blood bank conditions.

After the clotting factors have been extracted, the remaining insoluble fibrinogen can be converted in to a fibrin fabric. If the extracted cryoprecipitate is heated to about 50° C., it form a gel which can readily be formed into slabs which will harden further over 8-12 hr to form a tough membrane or fabric which can then be used to dress wounds. This dressing material will gradually be broken down and absorbed by the body.

BRIEF DESCRIPTION OF THE FIGURES

FIG. 1 is a flow diagram showing the extraction procedure of the present invention used to make a clotting factor concentrate and fibrin fabric.

DETAILED DESCRIPTION OF THE INVENTION

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a simple procedure for enhanced production of Factor VIII from collected plasma.

The traditional method for producing clotting factors, as well as many of the presently used methods, operates because many of the plasma proteins responsible for blood clotting precipitate (i.e., form cryoprecipitate) from solution at low temperatures. When a protein solution is frozen, ice crystals form and protein molecules, which are excluded from the ice crystals and become increasingly concentrated. Cooling or freezing the water also lowers the chemical activity of the water. Depending on the particular proteins, the proteins may actually fall out of solution, i.e., form a precipitate, if the protein more readily interacts with itself or with other proteins than with water. When the chemical activity of water is lowered such precipitation is favored.

Such precipitation may denature the proteins (make them irreversibly insoluble), so it is usual to freeze protein solutions rapidly and to a low temperature (i.e., −20° C. or lower) to minimize the formation of ice crystals and to prevent the growth of those crystals that do form. This is done to limit protein denaturation on ice crystal surfaces. Blood coagulation enzymes are extremely sensitive. Even when freezing is carried out with great care, ice crystals may cause "activation" of the prothrombin complex, resulting in spontaneous clot formation and loss of coagulation factors to proteolysis and/or clot formation.

The first step in the typical procedure for producing plasma cryoprecipitate is to centrifuge whole blood to separate the plasma from the red blood cells. This procedure is well known in the art and is often accomplished in special centrifuges that hold individual blood bags so that the plasma/red cell separation occurs without even opening the blood bag. Following the centrifugation, it is common practice to express the supernatant plasma into a "satellite" blood bag for further processing. Once the plasma is separated from red and white blood cells, the typical procedure is to rapidly freeze the plasma and to then slowly thaw the frozen plasma at about 4° C., during which thawing the clotting factors and other proteins form a cryoprecipitate which can be readily harvested by filtration or centrifugation. This cryoprecipitate is not rendered irreversibly insoluble and can be readily redissolved in a buffer, or even water, as is well known in the art.

Cryoprecipitation is generally believed to result when the removal of water from the immediate vicinity of the protein molecules causes the protein molecules to preferentially associate with each other rather than with water. This "removal" of water may represent changes in the solubility of the proteins with changes in temperature (i.e., water becomes less effective at dissolving the proteins). The process may also be accomplished or enhanced by using additives which "tie up" the water and cause it to interact with the proteins to a lesser degree. These additive substances can be any of a number of hydrophilic materials such as ethanol, polyethylene glycol, heparin, Pluronic RTM polyol polymers and various "salts" such as ammonium sulfate or ammonium acetate.

The "salting out" of proteins from solution is a classical biochemical procedure. These and other materials used to increase the yield of cryoprecipitate generally operate to decrease the effective activity of water in the mixture. That is, the water molecules preferentially interact with the added hydrophilic material instead of with the proteins. This permits the proteins to interact with each other and, therefore, precipitate from solution. Similarly, lowering the temperature—especially to the freezing point—also decreases the activity of water, allowing protein-protein interactions to predominate.

The hydrophilic additives just mentioned have the advantage of being relatively inexpensive and easy to use. However, their use usually necessitates additional washing steps to ensure that the additives are not carried over into the final product. Some additives may also damage or denature the labile clotting factors one is seeking to purify. As disclosed in U.S. Pat. No. 6,541,518 the present inventor has discovered that one of the agents frequently used as an anticoagulant in blood fractionation unexpectedly serves to enhance cryoprecipitate formation. The cryoprecipitate used in the present invention is preferably produced according to the methods of that patent by adding an increased amount of citrate prior to either freezing or chilling the plasma-citrate mixture. Alternatively, it is possible to add the additional citrate during the thawing of frozen plasma that has been anticoagulated with a lower amount of citrate.

For example, in one experiment five 40 ml aliquots of human plasma were brought to 10% wt/v trisodium citrate by the addition of 10 ml aliquots of a 50% wt/v trisodium citrate stock solution. After mixing the aliquots were stored for 24 hours at 4° C. At the end of this time a large white precipitate had formed in each sample. The samples were centrifuged at 1,500×g for 10 minutes in a refrigerated centrifuge to pellet the precipitate. To produce optimal single or limited donor pool clotting factor plasma is first collected to contain an optimal concentration of trisodium citrate. The optimum concentration is between 10% and 15% wt/vol. with about 12% wt/vol. being a preferred concentration in most cases. One means of collecting the plasma is to centrifuge freshly collected units of whole blood in a blood bag centrifuge as is well known to those of skill in the art. At that point the supernatant plasma can be expressed into a separate blood bag containing sufficient stock citrate solution (e.g., 50% wt/vol. trisodium citrate at pH 7.0 is convenient) to bring the final citrate concentration to the desired level. If a pool is to be made, several units of plasma can be expressed into a single large blood bag. Other means of achieving the same end will be apparent to those of ordinary skill in the art. For example, plasma collected by plasmapheresis can be collected directly into blood bags containing the extra citrate or the extra citrate can be added following collection.

The preferred method is to store the extra-citrated (10-15% wt/vol) plasma in the cold (4-7° C.) for 24 hours. During this time a heavy cryoprecipitate will form; after the cryoprecipitate has completely formed, it is separated from the supernatant plasma. Again, centrifugation of the blood bag is a good method of achieving this separation of cryoprecipitate and supernatant plasma although filtration of other methods may be used. Although cold precipitation is the preferred method, the plasma may also be frozen and the precipitation stage performed following thawing. The least preferred method is to freeze without added citrate and to add the citrate stock solution to the frozen plasma prior to or during thawing.

The clotting factors are essentially all present in the cryoprecipitate which, according to the prior art, can be redissolved in water or saline. However, merely redissolving the cryoprecipitate will produce a solution that is primarily fibrinogen. If sufficient amounts of this solution were administered to a patient to provide normal levels of clotting factors, the patient would receive a tremendous excess of protein mostly in the form of fibrinogen. Therefore, some method must be used to decrease the amount of fibrinogen relative to the Factor VIII. It is known in the art that extracting the cryoprecipitate with cold saline preferentially dissolves the clotting factors while leaving most of the cryoprecipitate (fibrinogen and fibronectin) as a solid precipitate. In earlier disclosures the present inventor improved upon this situation by extracting the cryoprecipitate with a high calcium (0.3M calcium chloride) buffer. This extraction dramatically reduced the extraction of fibrinogen so that a relatively high purity clotting factor concentrate could be produced in a single step. A drawback of that method, however, is that the concentrate containing such a high concentration calcium could not be directly administered to a patient. This necessitated the introduction of a calcium removal step.

The inventor has continued to investigate the method with an eye towards avoiding the additional calcium removal step. Now he has unexpected found that extraction of the cryoprecipitate with a cold solution of polyvinylpyrrolidone (PVP) (either in water or 0.9% saline) produces a clotting factor concentrate that is more pure without addition of calcium. Because PVP has long been used as a safe plasma expander and as a substitute for albumin, this improved concentrate can be directly administered to patients.

In an initial experiment was carried out by producing an aliquot of "super-cryoprecipitate" (high citrate cryoprecipitate made as explained above) and then extracting it with a number of different concentrations of PVP. There has been a limited amount of prior art use of PVP as an additive for increasing precipitation of proteins, but to the knowledge of the inventor PVP has not been used in extracting cryoprecipitate. Solutions of PVP ranging from 0% to 25% wt/vol were prepared (0%, 2.5%, 5%, 7.5%, 10%, 12.5%, 15%, 17.5%, 20% and 25%) were made in normal saline (0.9%). A soluble PVP of moderate molecular weight was used. An effective PVP is Kollidon PF12 (manufactured by BASF) soluble PVP (10K to 15K MW). An aliquot (10 ml) of each of these solutions was mixed with 10 ml of super-cryoprecipitate and mixed for 30 min at a temperature of 9° C. Then each mixture was centrifuged at 1500×g for 10 min to pellet any undissolved cryoprecipitate.

The 0% solution is the control solution for cold no PVP extraction. The solutions were then analyzed for Factor VIII content. The initial super-cryoprecipitate was assayed as containing Factor VIII at 6.3 units/ml (cryoprecipitate totally dissolved in warm buffer). Table 1 shows that the concentration of PVP had an effect on the amount of Factor VIII brought into solution. Note that the amount of Factor VIII was fairly constant as the concentration of PVP increases up to 12.5%. Thereafter, the amount of Factor VIII extracted begins to decrease. This is an indication that at low PVP concentrations, PVP has little effect on solubility of Factor VIII. As the concentration of PVP is increased a concentration is reached beyond which there is a fairly substantial decrease in Factor VIII solubility. However, PVP does not affect all proteins the same. An inspection of Fibrinogen concentration in mg/dl shows that as PVP concentration increases, there is a decrease in fibrinogen, then a plateau and then a further decrease in fibrinogen, While increasing PVP concentration initially has little effect on Factor VIII solubility, it does have a major effect on the solubility of other super-cryoprecipitate proteins—primarily fibrinogen. Further it is possible to select a PVP concentration that minimizes fibrinogen while maximizing Factor VIII.

TABLE 1

| PVP % | Units Factor VIII/ml | Fibrinogen mg/dl |
|---|---|---|
| 0% | 5.6 | 62 |
| 2.5% | 5.7 | 25 |
| 5% | 5.5 | 26 |
| 7.5% | 5.5 | 26 |
| 10% | 5.6 | 27 |
| 12.5% | 5.8 | 25 |
| 15% | 3.2 | 7 |
| 17.5% | 3.0 | 5 |
| 20% | 2.4 | 3 |
| 25% | 2.4 | 3 |

The inventive method of clotting factor production as diagrammed in FIG. 1 consists of first producing citrated cryoprecipitate. Preferably this is prepared from single donor plasma or from plasma pools produced from a limited number of donors. Ideally, the required concentration of citrate (10-15% wt./vol. trisodium citrate) is added as soon as practicable after plasma collection. Preferably, the citrated cryoprecipitate is collected after holding the plasma at about 4-6° C. for about 24 hours without freezing. It is also possible to freeze the plasma if it is not convenient to immediately effect separation of the citrated cryoprecipitate. In that case, the plasma is later thawed and held in the cold to allow complete formation of the cryoprecipitate. The cryoprecipitate is them separated from the supernatant by centrifugation or filtration. The supernatant plasma can be used for further fractionation or as a blood volume expander. The citrated cryoprecipitate is then extracted with the PVP extraction medium. This yields a clotting factor concentrate that can be used immediately in therapy. If desired citrate can be removed from the concentrate using chromatographic and ultrafiltration methods well known to those of skill in the art. Also, it is possible to use well known methods to further purify the concentrate if desired. Thus the present invention makes is possible for a blood bank to provide high quality clotting factor using simple equipment and procedures.

The undissolved material following low temperature PVP extraction is primarily fibrinogen (and fibronectin). It is possible to cause this material to gel if the temperature is raised to about 50° C. for about five minutes. At a lower temperature (i.e., room temperature) the material will eventually gel but heating above room temperature greatly accelerates the process. Most likely this is a clotting phenomenon mediated by one of the alternative coagulation pathways and can be potentiated by adding calcium ions. When the material gels, it forms a transparent semisolid which became increasingly opalescent and tough over the ensuing twelve hours. However, after 24 or so hours the material may begin to liquefy suggesting that the supernatant had contributed plasminogen which digested the fibrin.

This provides a simple method for preparing fibrin/fibrinogen membrane or fabric. After the clotting factor concentrate is withdrawn (e.g., in a sterile blood bag), it is possible to rinse the fibrinogen precipitate as necessary and mold it into a thin sheet all without opening the bag and compromising sterility. Once the fibrinogen has been properly molded, the bag can be heated to form the fibrin/fibrinogen fabric. Depending on the desired strength of the material, it can be allowed to "harden" for eight or so hours prior to use.

The fibrin/fibrinogen material can also be reinforced by embedding a mesh in the thin sheet. Because one of the advantages of the fibrin material is that it is ultimately absorbed by the body, it is advantageous to make any reinforcing mesh from a biodegradable or absorbable material such as those commonly used to produce absorbable suture material. While the preferred method is ideal for use by hospitals to prepare fibrin fabric immediately prior to surgery (possibly using autologous blood), it is also possible to lyophilize the fibrin fabric so that it can be produced in advance and at remote locations.

The following claims are to be understood to include what is specifically illustrated and described above, what can be obviously substituted and also what incorporates the essential idea of the invention. The illustrated embodiment has been set forth only for the purposes of example and that should not be taken as limiting the invention. Therefore, it is to be understood that, within the scope of the appended claims, the invention may be practiced other than as specifically described herein.

I claim:

1. A method for producing a factor VIII clotting factor concentrate from cryoprecipitate comprising the steps of:
    adding trisodium citrate to plasma to yield a concentration of trisodium citrate between 10% and 15% weight by volume;
    allowing cryoprecipitate to form in the plasma;
    separating the cryoprecipitate from the plasma by centrifugation;
    mixing the cryoprecipitate into a cold solution containing water and a concentration of 12.5% or less of soluble polyvinylpyrrolidone, to redissolve a portion of the cryoprecipitate; and
    separating an undissolved portion of the cryoprecipitate from the cold solution by centrifugation to obtain a separated cold solution, wherein the separated cold solution is the factor VIII clotting factor concentrate.

2. The method according to claim 1, wherein forming cryoprecipitate does not involve freezing the plasma.

3. The method according to claim 1, wherein the step of redissolving takes place at a temperature below about 10° C.

4. The method according to claim 1, wherein the step of adding trisodium citrate is accomplished by collecting the plasma directly into a container holding the trisodium citrate.

5. A method for producing a factor VIII clotting factor concentrate from cryoprecipitate comprising the steps of:
    adding trisodium citrate to plasma to yield a concentration of trisodium citrate of about 12% weight by volume;
    allowing cryoprecipitate to form in the plasma;
    separating the cryoprecipitate from the plasma by centrifugation;
    mixing the cryoprecipitate into a cold solution containing water and a concentration of 12.5% or less of soluble polyvinylpyrrolidone, to redissolve a portion of the cryoprecipitate; and
    separating an undissolved portion of the cryoprecipitate from the cold solution by centrifugation to obtain a separated cold solution, wherein the separated cold solution is the factor VIII clotting factor concentrate.

6. The method according to claim 5, wherein forming cryoprecipitate does not involve freezing the plasma.

7. The method according to claim 5, wherein the step of redissolving takes place at a temperature below about 10° C.

8. The method according to claim 5, wherein the step of adding trisodium citrate is accomplished by collecting the plasma directly into a container holding the trisodium citrate.

9. The method of claim 8, wherein the plasma is collected by plasmapheresis.

* * * * *